United States Patent
Yamada et al.

(10) Patent No.: US 9,605,291 B2
(45) Date of Patent: Mar. 28, 2017

(54) SUGAR-SOLUTION PRODUCTION METHOD

(71) Applicant: Toray Industries, Inc., Tokyo (JP)

(72) Inventors: Chiaki Yamada, Kamakura (JP); Hiroyuki Kurihara, Kamakura (JP); Katsushige Yamada, Kamakura (JP)

(73) Assignee: Toray Industries, Inc. (JP)

( * ) Notice: Subject to any disclaimer, the term of this patent is extended or adjusted under 35 U.S.C. 154(b) by 0 days.

(21) Appl. No.: 14/767,036

(22) PCT Filed: Feb. 19, 2014

(86) PCT No.: PCT/JP2014/053869
§ 371 (c)(1),
(2) Date: Aug. 11, 2015

(87) PCT Pub. No.: WO2014/129489
PCT Pub. Date: Aug. 28, 2014

(65) Prior Publication Data
US 2016/0010130 A1  Jan. 14, 2016

(30) Foreign Application Priority Data

Feb. 20, 2013  (JP) .................................. 2013-030631

(51) Int. Cl.
C12P 19/14 (2006.01)
C12P 19/02 (2006.01)

(52) U.S. Cl.
CPC .............. C12P 19/14 (2013.01); C12P 19/02 (2013.01)

(58) Field of Classification Search
CPC  C12N 9/2437; C12P 7/10; C13K 1/02; C13K 13/007; Y02E 50/16; C13B 20/165; C08B 1/003; C12Y 302/01004; C12M 47/10; C12R 1/645
See application file for complete search history.

(56) References Cited

U.S. PATENT DOCUMENTS

| | | |
|---|---|---|
| 2013/0157318 A1 | 6/2013 | Ishikawa et al. |
| 2013/0203117 A1 | 8/2013 | Kurihara et al. |
| 2015/0167037 A1 | 6/2015 | Yamada et al. |

FOREIGN PATENT DOCUMENTS

| | | |
|---|---|---|
| JP | 63-087994 A | 4/1988 |
| JP | 63-137691 A | 6/1988 |
| JP | 2011-041493 A | 3/2011 |
| JP | 4947223 B1 | 3/2012 |
| JP | 2012-100617 A | 5/2012 |
| JP | 2012-213375 A | 11/2012 |
| JP | 2014-054208 A | 3/2014 |
| WO | 2010/067785 A1 | 6/2010 |
| WO | 2010/110448 A1 | 9/2010 |
| WO | 2011/115039 A1 | 9/2011 |
| WO | 2011/115040 A1 | 9/2011 |
| WO | 2014/007189 | 1/2014 |

OTHER PUBLICATIONS

D.E. Otter et al., "Elution of *Trichoderma reesei* Cellulase From Cellulose by pH Adjustment With Sodium Hydroxide," Biotechnology Letters, vol. 6, No. 6 (1984), pp. 369-374.

Extended European Search Report dated Sep. 16, 2016, from corresponding European Patent Application No. 14754517.2.

*Primary Examiner* — Lynn Y Fan
(74) *Attorney, Agent, or Firm* — DLA Piper LLP (US)

(57) ABSTRACT

A method of producing a sugar solution includes (1) to (3): (1) preparing a slurry of a cellulose-containing biomass pretreated material and an inactivated cellulose, (2) hydrolyzing the slurry in (1) by adding a filamentous fungus-derived cellulase to the slurry, and (3) separating a hydrolysate in (2) into a solution component and a hydrolysis residue through solid-liquid separation, and filtering the solution component through an ultrafiltration membrane, thereby recovering the filamentous fungus-derived cellulase as a non-filtrate and the sugar solution as a filtrate.

5 Claims, 3 Drawing Sheets

FIG. 3 pH9.0  pH9.5  pH10.0  pH10.5  pH11.0  pH11.5

SUGAR-SOLUTION PRODUCTION METHOD

TECHNICAL FIELD

This disclosure relates to a method of producing a sugar solution from cellulose-containing biomass.

BACKGROUND

There have been many studies of methods that produce a sugar solution through hydrolysis of cellulose-containing biomass with cellulase, which uses little energy and is small in environmental load. However, the biggest problem of sugar solution producing methods using cellulase is the high manufacturing cost due to the high price of cellulase. Methods intended to recover and reuse cellulase after hydrolysis have been proposed to overcome such a technical drawback. However, there remains an issue of poor enzyme reusability attributed to the strong adsorption of cellulase to the hydrolysis residue generated during the hydrolysis of cellulose-containing biomass.

As methods that desorb the adsorbed cellulase from the hydrolysis residue to improve the cellulase recovery rate, a method that washes the hydrolysis residue with an alkaline aqueous solution of about pH 8 (D. E. Otter et al., "Elution of *Trichoderma reesei* Cellulase from Cellulose by pH Adjustment with Sodium Hydroxide," Biotechnology Letters (1984), Vol. 6, No. 6, 369-374), a method that adds a nonionic surfactant to the hydrolysate of cellulose-containing biomass (JP-A-63-87994) and the like are known. On the other hand, as methods that reduce the adsorption of cellulase to the hydrolysis residue, a method that adds water-soluble salts during the hydrolysis of cellulose-containing biomass to adjust the electrical conductivity of reaction liquid to 5 to 25 mS/cm (Japanese Patent No. 4947223), a method that adds calcium carbonate particles in an amount of 1 to 10 weight % based on the solid weight of cellulose-containing biomass (JP-A-2012-100617) and the like are known.

As described above, there have been attempts to reduce cellulase use through recovery and reuse of the cellulase used in the hydrolysis of cellulose-containing biomass. However, the problem remains unsolved because of the low recovery rate due to the strong adsorption of the cellulase to the hydrolysis residue.

It could therefore be helpful to provide a method of producing a sugar solution with which cellulase can be more efficiently recovered.

SUMMARY

We found that high efficiency recovery of the enzyme component of a filamentous fungus-derived cellulase is possible through addition of an inactivated cellulase during the hydrolysis of pretreated cellulose-containing biomass by a filamentous fungus-derived cellulase.

We thus provide [1] to [7]:
[1] A method of producing a sugar solution, comprising the following steps (1) to (3):
  (1) a step of preparing a slurry of a cellulose-containing biomass pretreated material and an inactivated cellulase;
  (2) a step of hydrolyzing the slurry in the step (1) by adding a filamentous fungus-derived cellulase to the slurry; and
  (3) a step of separating a hydrolysate in the step (2) into a solution component and a hydrolysis residue through solid-liquid separation, and filtering the solution component through an ultrafiltration membrane, thereby recovering the filamentous fungus-derived cellulase as a non-filtrate and the sugar solution as a filtrate.
[2] The method of producing a sugar solution according to [1], wherein the inactivated cellulase is an alkali-treated inactivated cellulase.
[3] The method of producing a sugar solution according to [1] or [2], wherein the inactivated cellulase is prepared by dipping the hydrolysis residue in the step (3) in an alkaline aqueous solution having a pH 11 or more.
[4] The method of producing a sugar solution according to [3], wherein the inactivated cellulase is prepared by dipping the hydrolysis residue in the step (3) in the alkaline aqueous solution of less than 65° C.
[5] The method of producing a sugar solution according to any one of [1] to [4], wherein the inactivated cellulase contains at least inactivated β-glucosidase.
[6] The method of producing a sugar solution according to any one of [1] to [5], wherein the slurry in the step (1) has a pH of 3.0 to 7.0.
[7] The method of producing a sugar solution according to any one of [1] to [6], wherein the filamentous fungus-derived cellulase is derived from an microorganism of genus *Trichoderma*.
[8] The method of producing a sugar solution according to any one of [1] to [7], wherein a pretreatment in the step (1) is a dilute sulfuric acid treatment.

The adsorption of a filamentous fungus-derived cellulase to the hydrolysis residue of pretreated cellulose-containing biomass can be inhibited. Specifically, it enables high efficient recovery and/or reuse of β-glucosidase, which plays an important role in hydrolysis reaction. As a result, the manufacturing cost of a sugar solution can be reduced.

BRIEF DESCRIPTION OF THE DRAWINGS

FIG. 3 is a diagram representing the relationship between the pH of the ammonia solution used for the dipping of a hydrolysis residue, and the amounts of inactivated cellulase recovered from the hydrolysis residue.

DETAILED DESCRIPTION

Figure 1:
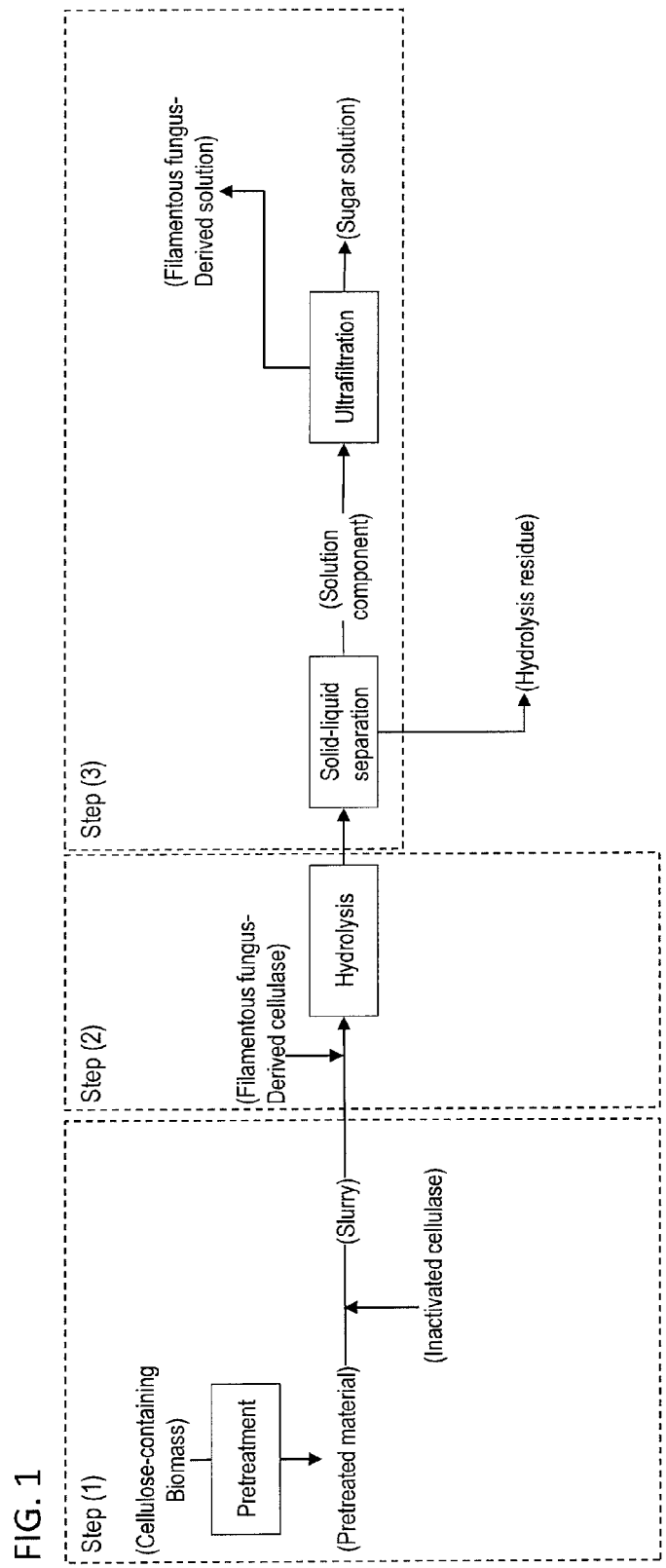
FIG. 1 is a schematic diagram representing an example of a sugar solution production method.
Figure 2:
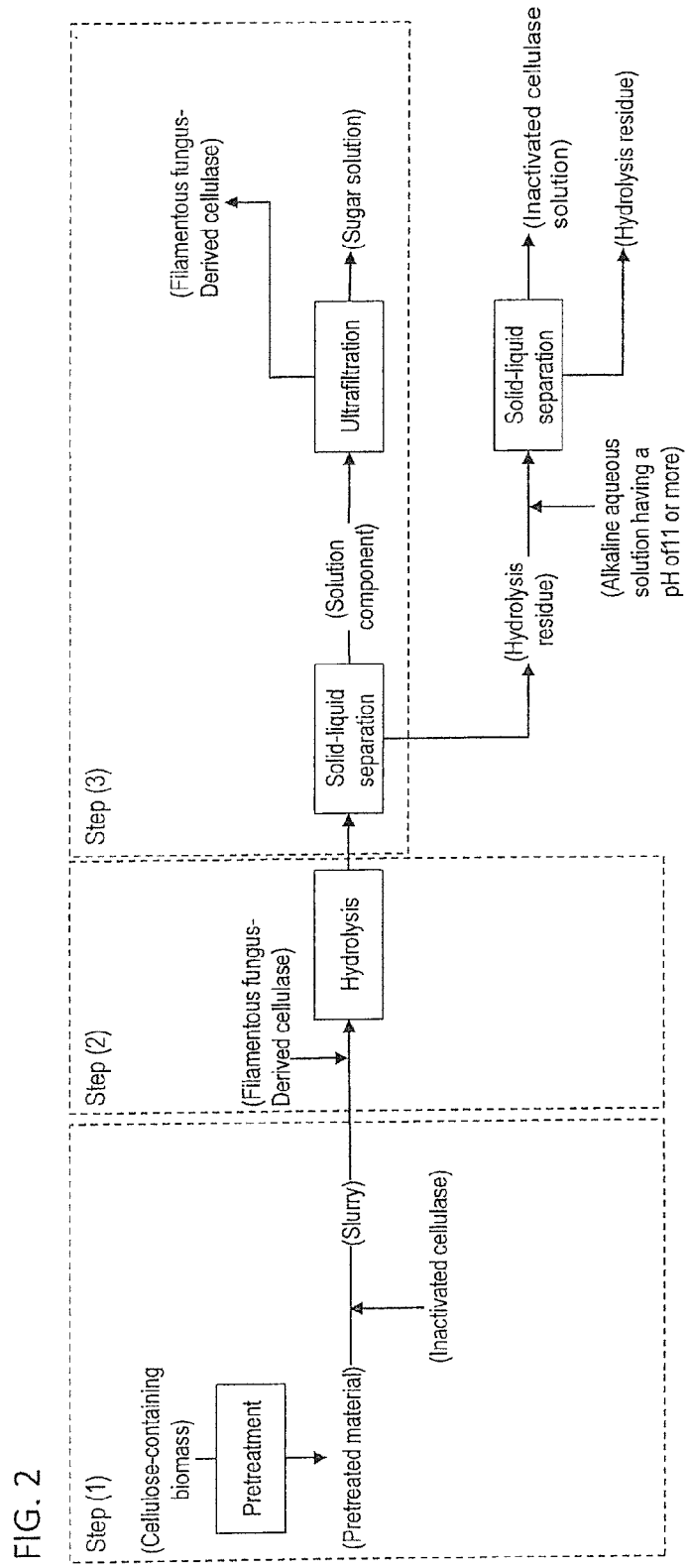
FIG. 2 is a schematic diagram representing an exemplary inactivated cellulase preparation method in a sugar solution production method.

An example of our method is described below with regard to each step.

Step (1): Step of Preparing a Slurry of a Cellulose-Containing Biomass Pretreated Material and an Inactivated Cellulase Examples of the cellulose-containing biomass include be herbaceous biomass such as bagasse, switchgrass, napier grass, erianthus, corn stover, beet pulp, cottonseed hull, palm empty fruit bunch, rice straw, wheat straw, bamboo, and bamboo grass, and ligneous biomass such as timber (e.g., white birch, and Japanese beech (*Fagus crenata*)), and scrap wood. In addition to cellulose and hemicellulose composed of sugars, the cellulose-containing biomass contains a lignin which is aromatic polymer or the like. The hydrolysis efficiency by cellulase can thus be improved by pretreating the cellulose-containing biomass.

Examples of the pretreatment method for the cellulose-containing biomass include an acid treatment with sulfuric acid or the like, an alkali treatment with caustic soda, ammonia or the like, a hydrothermal treatment, a subcritical water treatment, a pulverization treatment, and a steam treatment. Preferred for use in the sugar solution production method is a dilute sulfuric acid treatment because materials treated with dilute sulfuric acid best improve the reusability of a filamentous fungus-derived cellulase.

The cellulose-containing biomass pretreated material contains a solid component derived from the cellulose-containing biomass, and a solution component that contains xylose generated by the partial hydrolysis of the hemicellulose contained in the cellulose-containing biomass. The pretreated material may directly be used in subsequent steps, or may be used after removing the xylose-containing solution component by solid-liquid separation.

Inactivated cellulase is a cellulase which has lost enzymatic activity. As used herein, inactivated cellulase refers to cellulases with less than 10% remaining enzyme activity (β-glucosidase activity) after treatments that are performed to destabilize the protein structure such as a heat treatment, an alkali treatment, or an acid treatment. The method used to prepare the inactivated cellulase is not particularly limited, and the foregoing exemplary treatments may be used either alone or in combination. It is preferable to use an inactivated cellulase prepared by an alkali treatment. The deactivating temperature and pH of the cellulase depend on the kind of cellulase, and the denaturation conditions may be appropriately set according to the kind of the cellulase to be used.

The kind of the inactivated cellulase to be used is not particularly limited. It is, however, preferable that the inactivated cellulase is a filamentous fungus-derived cellulase to prevent adsorption of the filamentous fungus-derived cellulase to the pretreated material in the step (2) described below. Among the filamentous fungi-derived inactivated cellulase, β-glucosidase is highly effective, and the inactivated cellulase preferably contains at least an inactivated β-glucosidase.

Our methods reduce the manufacturing cost of a sugar solution, and a low-cost method is preferably used for the preparation of the inactivated cellulase. Specifically, it is preferable to prepare the inactivated cellulase by dipping the hydrolysis residue obtained in the below described step (3) in an alkaline aqueous solution having a pH 11 or more. This is preferable because the filamentous fungus-derived cellulase used for the cellulose hydrolysis is partially adsorbed to the hydrolysis residue from the step (3), and can be reused as the inactivated cellulase.

The temperature of dipping the hydrolysis residue into the alkaline aqueous solution is not particularly limited, as long as the filamentous fungus-derived cellulase adsorbed to the hydrolysis residue is desorbed and inactivated. However, the effects may not be fully obtained when the dipping temperature is excessively high because the inactivated cellulase desorbed from the hydrolysis residue undergoes heat decomposition. Thus, the dipping temperature is preferably less than 65° C.

The dipping time of the hydrolysis residue is not particularly limited. It is, however, preferable to dip the hydrolysis residue for 10 minutes to 6 hours, more preferably 30 minutes to 3 hours because the recovery of the inactivated cellulase may become insufficient when the dipping time is too short, and the inactivated cellulase may undergo heat decomposition when the dipping time is excessively long.

The dipping of the hydrolysis residue may be performed by using conventional methods. For example, the hydrolysis residue may be recovered to a dipping tank, and stirred after adding an alkaline aqueous solution. Alternatively, the hydrolysis residue may be dipped by passing an alkaline aqueous solution through a pressure filtration device after solid-liquid separation, as described in WO 2011/115039.

The solid concentration of the slurry containing the cellulose-containing biomass pretreated material and the inactivated cellulase is not particularly limited, however, is preferably 1 to 30 weight %. When the concentration of the solid matter is low, the concentration of sugar generated by the hydrolysis is low, and thus, such a case may not be suitable to provide a raw fermentation material. On the other hand, when the concentration is excessively high, handling may be difficult.

Step (2): Step of Hydrolyzing the Slurry in the Step (1) by Adding a Filamentous Fungus-Derived Cellulase to the Slurry A filamentous fungus-derived cellulase is used for the hydrolysis of the cellulose-containing biomass. Examples of the filamentous fungus include microorganisms of the genera *Trichoderma, Aspergillus, Cellulomonas, Clostridium, Streptomyces, Humicola, Acremonium, Irpex, Mucor*, and *Talaromyces*. The cellulase may be of mutant strains of improved cellulase productivity obtained by treating these microorganisms with a mutagen or by UV irradiation.

Preferred for use as the filamentous fungus is the genus *Trichoderma* for its ability to produce large quantities of an enzyme component of high specific activity in a culture for cellulose hydrolysis. Specific examples of the genus *Trichoderma*-derived cellulases include cellulases derived from *Trichoderma reesei* QM 9414, *Trichoderma reesei* QM 9123, *Trichoderma reesei* Rut C-30, *Trichoderma reesei* PC 3-7, *Trichoderma reesei* CL-847, *Trichoderma reesei* MCG 77, *Trichoderma reesei* MCG 80, and *Trichoderma viride* QM 9123. Particularly preferred are cellulases derived from *Trichoderma reesei*.

The filamentous fungus-derived cellulase is an enzyme composition having an activity to produce monosaccharides such as glucose and xylose through hydrolysis of cellulose and/or hemicellulose, and preferably contains at least one enzyme component selected from the group consisting of cellobiohydrolase, endoglucanase, β-glucosidase, xylanase, and β-xylosidase. Examples of such enzyme components of *Trichoderma reesei*-derived cellulase include cellobiohydrolase I, cellobiohydrolase II, endoglucanase I, endoglucanase III, β-glucosidase, xylanase, and β-xylosidase. These are preferred because these enzyme components produce synergy or complement each other to enable more efficient hydrolysis of cellulose and/or hemicellulose.

Cellobiohydrolase is a collective name for enzymes that release cellobiose through hydrolysis of cellulose chains, and a group of enzymes with the EC number EC 3.2.1.91 has been described as belonging to cellobiohydrolase. Cellobiohydrolase I starts the hydrolysis reaction from the reducing end of a cellulose chain, whereas cellobiohydrolase II starts the hydrolysis reaction from the non-reducing end.

Endoglucanase is a collective name for enzymes that hydrolyze a cellulose chain from the middle, and a group of enzymes with the EC number EC 3.2.1.4 has been described as belonging to endoglucanase.

β-Glucosidase is a collective name for enzymes that act on cellooligosaccharide or cellobiose, and a group of enzymes with the EC number EC 3.2.1.21 has been described as belonging to β-glucosidase.

Xylanase is a collective name for enzymes that act on hemicellulose, or particularly xylan, and a group of enzymes with the EC number EC 3.2.1.8 has been described as belonging to xylanase.

β-Xylosidase is a collective name for enzymes that act on xylooligosaccharide, and a group of enzymes with the EC number EC 3.2.1.37 has been described as belonging to β-xylosidase.

These cellulase components may be separated by using conventional techniques such as gel filtration, ion exchange, and two-dimensional electrophoresis, and may be identified by comparing the amino acid sequences of the separated components with database. Conventional analytical techniques such as N-terminal analysis, C-terminal analysis, and mass spectrometry may be used for the analysis of the amino acid sequences.

The enzyme activity of the filamentous fungus-derived cellulase can be evaluated from polysaccharide hydrolysis activity such as Avicel degradation activity, carboxymethyl cellulose (CMC) degradation activity, cellobiose degradation activity, xylan degradation activity, and mannan degradation activity. An enzyme that shows Avicel degradation activity is primarily cellobiohydrolase that hydrolyzes from terminal portions of cellulose. An enzyme that shows cellobiose degradation activity is primarily β-glucosidase. Enzymes involved in CMC degradation activity are primarily cellobiohydrolase and endoglucanase. Enzymes that show xylan degradation activity are primarily xylanase and β-xylosidase. As used herein, the word "primarily" means that the enzyme has the highest involvement in the degradation concerned, and the term does not exclude the involvement of other enzyme components in the degradation.

Filamentous fungi produce cellulase in a culture, and the culture may be directly used as a crude enzyme agent, or the enzyme group may be purified by using a conventional method and used as a preparation in the form of a filamentous fungus-derived cellulase mixture. When the filamentous fungus-derived cellulase is purified and used as a preparation, non-enzyme components such as a protease inhibitor, a dispersant, a dissolution promoter, and a stabilizer may be added. Preferred is a crude enzyme material. A crude enzyme material originates in the culture supernatant of a filamentous fungus culture grown for the desired time period in a medium adjusted for cellulase production. The medium components to be used are not particularly limited, and a medium supplemented with cellulose may generally be used to promote cellulase production. Preferably, the crude enzyme material to be used may be the culture itself, or may be a culture supernatant obtained by simply removing the *Trichoderma*.

The weight ratio of each enzyme component in the crude enzyme material is not particularly limited. For example, a *Trichoderma reesei*-derived culture contains 50 to 95 weight % of cellobiohydrolase, and the other components include endoglucanase and β-glucosidase. Although the genus *Trichoderma* produces a strong cellulase component in a culture, the β-glucosidase activity is weak because a large proportion of β-glucosidase is retained inside the cell or on the surface of the cell membrane. It is therefore possible to add β-glucosidase of the same or different kind to the crude enzyme material. Preferred as the β-glucosidase of different kind is the genus *Aspergillus*-derived β-glucosidase. Examples of the genus *Aspergillus*-derived β-glucosidase include the Novozyme 188 commercially available from Novozymes. It is also possible to use a culture of improved β-glucosidase activity prepared by introducing a β-glucosidase gene into the microorganism of the genus *Trichoderma* and cultivating the microorganism of the genus *Trichoderma* which has been subjected to genetic recombination so that the β-glucosidase is produced in the culture.

When the genus *Trichoderma*-derived cellulase is used, the hydrolysis reaction temperature is preferably 40 to 60° C., more preferably 45 to 55° C. The hydrolysis reaction time is preferably from 2 hours to 200 hours. When the hydrolysis reaction time is less than 2 hours, a sufficient amount of sugar may not be obtained. When the hydrolysis reaction time is longer than 200 hours, inactivation of the cellulase may be promoted, and an adverse effect on reusability of the recovered cellulase may be caused.

The pH of the slurry prepared in the step (1) for hydrolysis, specifically the pH in the hydrolysis reaction is preferably 3.0 to 7.0, more preferably 4.0 to 6.0. When the filamentous fungus-derived cellulase is the genus *Trichoderma*-derived cellulose, the optimum reaction pH is 5.0. Against the pH changes that occur during the hydrolysis, it is preferable to perform the reaction by maintaining the pH constant with addition of a buffer to the reaction liquid, or with the use of an acid or an alkali.

Step (3): Step of Separating a Hydrolysate in the Step (2) into a Solution Component and a Hydrolysis Residue Through Solid-Liquid Separation, and Filtering the Solution Component Through an Ultrafiltration Membrane, Thereby Recovering the Filamentous Fungus-Derived Cellulase as a Non-Filtrate and the Sugar Solution as a Filtrate The solution component obtained through solid-liquid separation of the hydrolysate in the step (2) contains a filamentous fungus-derived cellulase component and a sugar component. These can be separated from each other by filtration through an ultrafiltration membrane.

An ultrafiltration membrane, also called UF membrane, is a membrane with a molecular weight cut-off of 500 to 200,000. The pore size in the membrane surface of a ultrafiltration membrane is too small to measure with an electron microscope or the like, and the value of molecular weight cut-off is used as an index of pore size, instead of an average pore size. Molecular weight cut-off is well known in the art as an index of ultrafiltration membrane performance, as described in page 92 of Membranology Experiment Series, Vol. III, Artificial Membrane, The Membrane Society of Japan, Members of Editorial Board: Shouji KIMURA, Shinichi NAKAO, Haruhiko OOYA, Tsutomu NAKAGAWA (1993, Kyoritsu Shuppan), which contains the passage "a molecular weight cut-off curve is a graph obtained by plotting the molecular weight of a solute on the horizontal axis against the percentage retention taken on the vertical axis. The molecular weight which the blocking rate reaches 90% is referred to as the molecular weight cut-off of the membrane."

In the ultrafiltration membrane separation of the filamentous fungus-derived cellulase component and the sugar component, the molecular weight cut-off is not particularly limited, as long as it allows for passage of the glucose (molecular weight of 180) and the xylose (molecular weight of 150) contained as the main component monosaccharides of the sugar solution while retaining the filamentous fungus-derived cellulase. However, the molecular weight cut-off is preferably 500 to 50,000, and is more preferably 5,000 to 50,000, further preferably 10,000 to 30,000 from the standpoint of enzyme separation from the other substances that show inhibitory effect against the enzyme reaction.

Examples of the usable materials of the ultrafiltration membrane include polyethersulfone (PES), polysulfone (PS), polyacrylonitrile (PAN), polyvinylidene fluoride (PVDF), regenerated cellulose, cellulose, cellulose ester, sulfonated polysulfone, sulfonated polyethersulfone, polyolefin, polyvinyl alcohol, polymethylmethacrylate, and polytetrafluoroethylene. However, preferred as the ultrafiltration membrane are materials containing synthetic polymers such as PES and PVDF, because regenerated cellulose, cellulose, and cellulose ester undergo degradation by cellulase.

The ultrafiltration membrane may be of a form as may be appropriately selected from, for example, a flat, a spiral, a tubular, and a hollow fiber membrane. Specific examples thereof include the type G-5, G-10, G-20, G-50, PW, and HWSUF available from DESAL; HFM-180, HFM-183, HFM-251, HFM-300, HFK-131, HFK-328, MPT-U20, MPS-U20P, and MPS-U20S available from KOCH; SPE1, SPE3, SPE5, SPE10, SPE30, SPV5, SPV50, and SOW30 available from Synder; MICROZA (registered trademark) UF series of sizes equivalent of the molecular weight cut-off of 3,000 to 10,000, available from Asahi Kasei Corporation; and NTR7410 and NTR7450 available from Nitto Denko Corporation.

The filamentous fungus-derived cellulase to be recovered as the non-filtrate with the ultrafiltration membrane can be reused for the hydrolysis of the cellulose-containing biomass. Our methods enable reducing cellulase use through reuse of the recovered cellulase, and reducing the manufacturing cost of the sugar solution. In the hydrolysis of the cellulose-containing biomass with the recovered cellulase, the recovered cellulase alone may not be enough to obtain a sufficient sugar yield. In such cases, an unused filamentous fungus-derived cellulase may be newly added to the recovered cellulase. Such an unused filamentous fungus-derived cellulase should preferably be added in the least required amount for obtaining a sufficient sugar yield to avoid the cost increase due to the addition of the unused filamentous fungus-derived cellulase.

The main components of the sugar solution to be recovered as the filtrate with the ultrafiltration membrane are xylose and glucose, which are monosaccharide, and the sugar solution may directly be used as the raw material of the fermentation in the below described fermentation step. However, a concentration process that increases the sugar concentration may additionally be performed to improve the efficiency of the fermentation step. The sugar solution may be concentrated by using processes such as evaporative concentration, vacuum concentration, and membrane concentration. However, a concentrated sugar solution with concentrated sugar components can be obtained by filtration through a nanofiltration membrane and/or a reverse osmosis membrane, which involve low energy use, and enable separation of the fermentation inhibitor contained in the sugar solution, as described in WO 2010/067785.

Various chemicals can be produced by growing microorganisms capable of producing chemicals from the fermentation raw material provided by the obtained sugar solution. As used herein, "growing microorganisms with the fermentation raw material" means allowing microorganisms to proliferate, grow, and maintain themselves with the nutrients provided by the sugar components or amino source contained in the sugar solution. Specific examples of the chemicals include materials mass-produced in fermentation industry such as alcohols, organic acids, amino acids, and nucleic acids. These chemicals are produced by using the sugar components in the sugar solution as the carbon source, and accumulate inside and outside of an organism through its metabolism. Specific examples of chemicals that can be produced by microorganisms include alcohols such as ethanol, 1,3-propanediol, 1,4-butanediol, and glycerol; organic acids such as acetic acid, lactic acid, pyruvic acid, succinic acid, malic acid, itaconic acid, and citric acid; nucleosides such as inosine, and guanosine; nucleotides such as inosinic acid and guanylic acid; and amine compounds such as cadaverine. The sugar solution may also be used for the production of, for example, enzymes, antibiotics, and recombinant proteins. The microorganisms to be used for the production of such chemicals may be any microorganisms that are capable of efficiently producing chemicals of interest, and may be, for example, *Escherichia coli*, yeasts, filamentous fungi, and basidiomycetes.

EXAMPLES

Our methods are described below in greater detail using Examples. This disclosure, however, is not limited by these.

Reference Example 1

Preparation of Cellulose-Containing Biomass Pretreated Material

Cellulose-containing biomass (corncob) was dipped in a 1% aqueous solution of sulfuric acid used in two times the weight of the biomass, and was processed in an autoclave (Nitto Koatsu KK) at 150° C. for 30 minutes, thereby obtaining a cellulose-containing biomass pretreated material. The material was used in the Examples below.

Reference Example 2

Protein Concentration Measurement

The protein concentration was measured with a commercially available protein concentration measurement reagent (Quick Start Bradford Protein Assay, Bio-Rad). A diluted cellulase solution (5 µL) was added to 250 µL of the protein concentration measurement reagent that had been brought back to room temperature, and the absorbance at 595 nm was measured with a microplate reader (POWERSCAN HT, Dainippon Sumitomo Pharma Co., Ltd.) after allowing to stand at room temperature for 5 minutes. A bovine serum albumin aqueous solution was used as the standard, and the protein concentration of the cellulase solution was calculated on a standard curve.

Reference Example 3

β-Glucosidase Activity Measurement

The activity of the filamentous fungus-derived cellulase was measured by using the β-glucosidase activity as an index, as follows.

An enzyme solution (0.1 mL) was added to 0.9 mL of a 55 mM acetate buffer (pH 5.0) containing 1.1 mM of 4-nitrophenyl-β-D-glucopyranoside, and the mixture was allowed to react at 30° C. (substrate final concentration 1 mM, buffer final concentration 50 mM). After accurately 10 minutes of reaction, a 2M sodium carbonate aqueous solution (0.1 mL) was added to quench the reaction, and the absorbance at 405 nm was measured (OD test). As a blank, the same absorbance measurement at 405 nm was performed for a sample that had been prepared by serially adding a 2M sodium hydrogen carbonate aqueous solution and an enzyme solution to a substrate solution (OD blank). The amount of enzyme that generates 1 µmol of 4-nitrophenol per minute in the foregoing reaction system was defined as 1 U, and the activity value (U/mL) was calculated according to the following equation. The millimolar molecular extinction coefficient of the 4-nitrophenol in the foregoing reaction system is 17.2 L/mmol/cm.

β-Glucosidase activity (U/mL)={(OD test−OD blank)×1.1 (mL)×enzyme dilution factor}/ {17.2×10 (min)×0.1 (mL)}

Reference Example 4

Cellulase Recovery from Hydrolysate of Cellulose-Containing Biomass

Step 1: Preparation of Slurry of Cellulose-Containing Biomass Pretreated Material The cellulose-containing biomass pretreated material (1.0 g, absolute dry weight) prepared in the manner described in Reference Example 1 was weighed into a 50-mL centrifuge tube, and suspended in 7.0 mL of water. The measured pH was 2.3. A 10% ammonia solution was added until the slurry pH reached 5.0, and water was added to make the total weight 10 g. The resulting slurry had a solid concentration of 10%.

Step 2: Hydrolysis by Filamentous Fungus-Derived Cellulose

A commercially available cellulase enzyme solution (ACCELLERASE® DUET; manufactured by Genencor) was used as the filamentous fungus-derived cellulase. The cellulase enzyme solution had a protein concentration of 40 g/L as measured according to the method described in Reference Example 2. The cellulase enzyme solution (0.2 mL) was added to the slurry prepared in the step (1), followed by mixing under rotation at 50° C. for 24 hours with a hybridization rotator (SN-06BN, manufactured by Nisshinrika).

Step 3: Recovery of Filamentous Fungus-Derived Cellulase and Sugar Solution

The hydrolysate from the step 2 was centrifuged (8,000 G, 10 minutes) for solid-liquid separation, and a supernatant (8 g) and a hydrolysis residue (2 g) were obtained. The hydrolysis residue was resuspended in 8 mL of water, and centrifuged (8,000 G, 10 minutes) again, thereby recovering the remaining solution component in the hydrolysis residue. The recovered supernatants were combined, and passed through a 0.22-μm microfiltration membrane (MILLEX-GV, made of hydrophilic PVDF; MerckMillipore) to remove fine particles. The solution was then filtered through an ultrafiltration membrane (VIVASPIN20, made of PES; Sartorius stedim biotech) with a molecular weight cut-off of 10,000. This was subjected to centrifugal filtration performed at 8,000 G until the non-filtrate became 1 mL or less, and the non-filtrate was diluted for desalting at least 10 times with ultrapure water. After performing centrifugal filtration at 8,000 G until the non-filtrate became about 1 mL, the filtrate was recovered as a sugar solution, and the non-filtrate was recovered as a recovered cellulase solution.

Reference Example 5

Preparation of Inactivated Cellulase by Alkali Treatment

A cellulase enzyme solution (0.1 mL, "ACCELLERASE® DUET," manufactured by Genencor) was added to 7.0 mL of an ammonia solution (pH 11.0), and the mixture was maintained at 50° C. for 1 hour, thereby preparing an inactivated cellulase solution. The inactivated cellulase was measured for β-glucosidase activity according to the method described in Reference Example 3. The measurement did not detect any activity, confirming that the β-glucosidase activity was quenched 100%.

Reference Example 6

Preparation of Inactivated β-Glucosidase by Alkali Treatment

Aspergillus niger-derived β-glucosidase (0.075 mL; E-BGLUC, manufactured by Megazyme) was added to 1.0 mL of an ammonia solution (pH 11.0), and the mixture was allowed to stand for 1 hour under about 25° C. room temperature, thereby preparing an inactivated β-glucosidase solution. The inactivated β-glucosidase solution was measured for activity according to the method described in Reference Example 3. The remaining activity was 2.1% of the activity before treatment, confirming that an inactivated β-glucosidase was produced.

Reference Example 7

Preparation of Inactivated Cellulase by Dipping Hydrolysis Residue in Alkaline Aqueous Solution A sugar solution was produced in the manner described in Reference Example 4. The hydrolysis residue was suspended in 7.0 mL of an ammonia solution (pH 11.0 or 11.5), followed by mixing under rotation at about 25° C. room temperature. After 1 hour, the mixture was centrifuged (8,000 G, 10 minutes), and the supernatant was recovered as an inactivated cellulase solution. The solution was measured for β-glucosidase activity according to the method described in Reference Example 3. The measurement did not detect any activity, confirming that the β-glucosidase activity was disappeared 100%.

Comparative Example 1

Recovery of Enzyme from Cellulose-Containing Biomass Hydrolysate Containing No Inactivated Cellulase A sugar solution was produced in the manner described in Reference Example 4, and a recovered cellulase solution was obtained. However, water or an ammonia solution (pH 11.0) was used for the preparation of the slurry (pH 5.0) with a solid concentration of 10% in the step (1). The recovered cellulase solution was measured for activity in the same manner as in Reference Example 3.

Example 1

Recovery of Enzyme from Cellulose-Containing Biomass Hydrolysate Containing Inactivated Cellulase A slurry (pH 5.0) having a solid concentration of 10% was prepared in the same manner as in the step (1) of Reference Example 4, except that the inactivated cellulase solution prepared in Reference Example 5 or 7, or the inactivated β-glucosidase solution prepared in Reference Example 6 was used instead of water. A sugar solution was produced, and a recovered cellulase solution was obtained in the same manner as in Reference Example 4. The recovered cellulase solution was measured for activity in the manner described in Reference Example 3.

The enzyme activities of the recovered cellulase solutions of Comparative Example 1 and Example 1 are summarized as relative activities in Table 1 below. The enzyme activities of the recovered cellulase solutions greatly improved by addition of the inactivated cellulase or inactivated β-glucosidase.

TABLE 1

|  | Solution used for slurry preparation | Relative activity of recovered cellulase liquid |
|---|---|---|
| Comparative Example 1 | Water | 1.0 (reference) |
|  | Ammonia solution (pH 11.0) | 1.0 |
| Example 1 | Inactivated cellulase solution (Reference Example 5) | 49 |
|  | Inactivated β-glucosidase solution (Reference Example 6) | 58 |
|  | Inactivated cellulase solution (Reference Example 7, pH 11.0) | 48 |
|  | Inactivated cellulase solution (Reference Example 7, pH 11.5) | 53 |

Example 2

Effect of pH on Dipping of Hydrolysis Residue on Inactivated Cellulase Recovery

Figure 3:
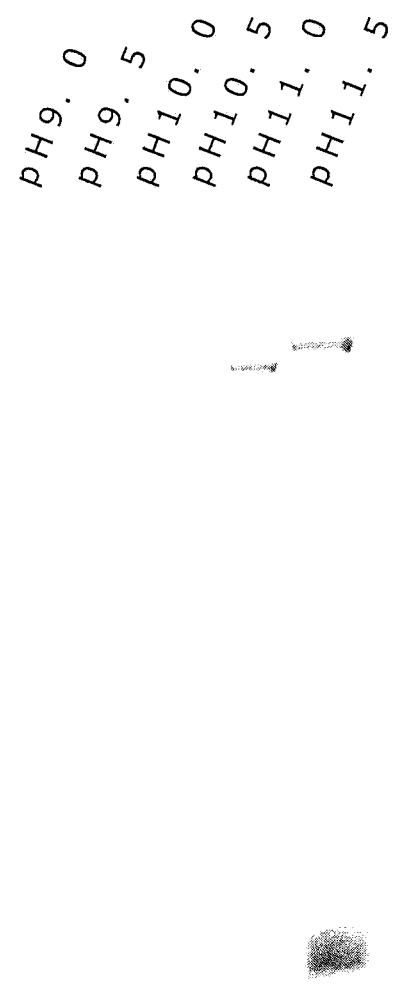

Water, or an ammonia solution having a pH of 9.0 to 11.5 was used for the dipping of the hydrolysis residue in Reference Example 7, and the supernatant was recovered. The amount of filamentous fungus-derived cellulase contained in the supernatant was then determined by SDS polyacrylamide electrophoresis (SDS-PAGE) [standard mini-slab size gel of 15% gel concentration (e-PAGEL E-T/R15L, manufactured by Atto); the sample was applied in 5 μL, 20 mA, 75 min] (FIG. 3). When an ammonia solution having a pH of 11.0 or more was used, a large amount of elution of the filamentous fungus-derived cellulase from the hydrolysis residue was confirmed.

To examine the enzyme component contained in the inactivated cellulase solution, the most major band in the inactivated cellulase of pH 11.0 and pH 11.5 was cut, and the peptides obtained by in-gel digestion with trypsin were used for LC-MS/MS mass spectrometry. A Mascot search of peptide mass data conducted for protein identification revealed that the most abundant protein was cellobiohydrolase I in the inactivated cellulase of pH 11.0, and β-glucosidase in the inactivated cellulase of pH 11.5. The same procedure was used for the second most major band cut from the inactivated cellulase of pH 11.0. The protein was identified as β-glucosidase, confirming that β-glucosidase was contained in the both inactivated cellulases.

Because the amount of eluted filamentous fungus-derived cellulase depends on the pH of the ammonia solution, whether the eluted filamentous fungus-derived cellulase was inactivated cellulase was determined by dissolving 0.1 mL of the cellulase enzyme solution in 7 mL of the ammonia solution having each pH, and finding whether the remaining activity was less than 10% after a 1-hour alkali treatment performed at about 25° C. room temperature. The activities of the alkali treated solutions are shown in Table 2. The remaining activity became less than 10% at a pH of 10.5 or more, and it was confirmed that inactivated cellulases were obtained in this pH range.

TABLE 2

| pH of Ammonia solution | Activity (U/mL) | Remaining activity (%) |
|---|---|---|
| Untreated | 1.70 | 100 |
| 9.0 | 1.59 | 93.3 |
| 9.5 | 1.01 | 59.6 |
| 10.0 | 0.43 | 25.5 |
| 10.5 | 0.04 | 2.3 |
| 11.0 | Undetected | 0 |
| 11.5 | Undetected | 0 |

Example 3

Effect of Dipping Temperature of Hydrolysis Residue

An ammonia solution having a pH of 11.0 was used, and the hydrolysis residue was dipped in a temperature range of about 25° C. room temperature to 95° C. in Reference Example 7. The resulting inactivated cellulase solution was subjected to SDS-PAGE in the same manner as in Example 2. The inactivated cellulase band gradually became blurred at 65° C. or more, suggesting that degradation had occurred.

Example 4

Effect of Kind of Alkali Used for Dipping of Hydrolysis Residue

An inactivated cellulase solution was prepared by using an aqueous solution (pH 11.0) of sodium hydroxide, potassium hydroxide, calcium hydroxide, calcium carbonate, or trisodium phosphate for the dipping of the hydrolysis residue in Reference Example 7. A recovered cellulase solution was obtained in the same manner as in Example 1 other than the above, and the activity was measured according to the method described in Reference Example 3. The results are shown as relative activities in Table 3. The recovered cellulase solution prepared by using any of the alkalis had the same level of relative activity as the solution using ammonia.

TABLE 3

|  | Alkaline aqueous solution | Inactivated cellulase | Relative activity of recovered cellulase solution |
|---|---|---|---|
| Comparative Example 1 | Ammonia solution | − | 1.0 (reference) |
| Example 1 | Ammonia solution | + | 48 |
| Example 4 | Sodium hydroxide aqueous solution | + | 47 |
|  | Potassium hydroxide aqueous solution | + | 48 |
|  | Calcium hydroxide aqueous solution | + | 46 |
|  | Sodium carbonate aqueous solution | + | 49 |

TABLE 3-continued

| Alkaline aqueous solution | Inactivated cellulase | Relative activity of recovered cellulase solution |
|---|---|---|
| Calcium carbonate aqueous solution | + | 48 |
| Trisodium phosphate aqueous solution | + | 47 |

INDUSTRIAL APPLICABILITY

The obtained sugar solution can be used as a raw sugar material of various fermentation products.

The invention claimed is:

1. A method of producing a sugar solution, comprising (1) to (3):
  (1) preparing a slurry of a cellulose-containing biomass pretreated material and an inactivated cellulase;
  (2) hydrolyzing the slurry in (1) by adding a filamentous fungus-derived cellulase to the slurry; and
  (3) separating a hydrolysate in (2) into a solution component and a hydrolysis residue through solid-liquid separation, and filtering the solution component through an ultrafiltration membrane, thereby recovering the filamentous fungus-derived cellulase as a non-filtrate and the sugar solution as a filtrate, wherein the inactivated cellulase in (1) is prepared by dipping the hydrolysis residue in (3) in an alkaline aqueous solution selected from a group consisting of ammonia, sodium hydroxide, potassium hydroxide, calcium hydroxide, calcium carbonate, sodium carbonate, and trisodium phosphate, having a pH 11 or more and a temperature of less than 65° C., and wherein the inactivated cellulase is used in (1) of the next and later production process.

2. The method according to claim 1, wherein the inactivated cellulase contains at least inactivated β-glucosidase.

3. The method according to claim 1, wherein the slurry in (1) has a pH of 3.0 to 7.0.

4. The method according to claim 1, wherein the filamentous fungus-derived cellulase is derived from a microorganism of genus *Trichoderma*.

5. The method according to claim 1, wherein the pretreatment in (1) is a dilute sulfuric acid treatment.

* * * * *